United States Patent [19]

Chaney

[11] Patent Number: 4,539,980
[45] Date of Patent: Sep. 10, 1985

[54] MALE ORGAN CONDITIONER

[76] Inventor: John L. Chaney, 156 Broad St., Box 592, Lake Geneva, Wis. 53147

[21] Appl. No.: 530,523

[22] Filed: Sep. 9, 1983

[51] Int. Cl.³ .............................................. A61F 5/00
[52] U.S. Cl. ................................... 128/79; 128/303 A
[58] Field of Search ............... 128/79, 303 A, 325–327

[56] References Cited

U.S. PATENT DOCUMENTS

| 2,619,964 | 12/1952 | Thaete | 128/303 A |
|---|---|---|---|
| 2,942,604 | 6/1960 | Gravlee | 128/303 A |
| 3,455,301 | 7/1969 | Clark | 128/79 |
| 3,461,863 | 8/1969 | Sullinger | 128/79 |
| 3,759,253 | 9/1973 | Cray | 128/79 |
| 4,224,933 | 9/1980 | Reiling | 128/79 |

FOREIGN PATENT DOCUMENTS 2057734  6/1972  Fed. Rep. of Germany ........ 128/79

Primary Examiner—Dalton L. Truluck
Attorney, Agent, or Firm—Fuller, House & Hohenfeldt

[57] ABSTRACT

A central elastic ring having elastic loops attached to opposite sides. The loops are of sufficient size to insert fingers on opposite hands into them whereupon when the hands are spread away from each other the elastic ring enlarges for being set on the root of a penis. When released the ring contracts to act as a check valve for enabling blood to be massaged into the penis and to prevent its outflow to thereby obtain and maintain an erection. An accessory provides for mounting the elastic ring on a rigid sleeve which can be fitted over the penis so the elastic ring can be slid off at the root of the penis.

8 Claims, 7 Drawing Figures

MALE ORGAN CONDITIONER

BACKGROUND OF THE INVENTION

This invention relates to a device for assisting a male to obtain and maintain an erection of his penis to enable performing sexual intercourse.

Medical literature reveals that males at all ages sometimes inexplicably lose the capability of obtaining an erection for a variety of reasons and even without apparent reasons. In some cases there are psychological causes and in other cases physiological causes underlying the inability to obtain or maintain an erection. Regardless of the cause of impotency, however, in most cases the male maintains the desire and urge to indulge in intercourse.

Development of a penile erection is, of course, dependent on a complex interaction of psychological and physiological factors which are not clearly understood but the anatomical phenomena associated with successful erection are well known. The penis is composed of erectile tissue arranged in three longitudinal columns bonded by fibrous tissue. Erectile tissue has a spongelike structure containing cavernous spaces for being occupied by blood. These spaces are fed by arterioles and capillaries and are drained by small flow restricting veins. Muscle fibers traverse the walls of the spaces and surround their discharge veins. When the penis is induced to erect, arterioles feeding the spaces dilate, the muscle fibers around the spaces relax, and the muscle controlling the venous outlets contract to restrict blood discharge from the caverns. The cavernous spaces in the erectile tissue expand as blood is pumped through them at high pressure and the penis becomes hard and erect. Thus, the natural erection process is basically a matter of capturing and holding pressurized blood in the cavernous tissues of the penis.

Surgically implantable devices have been developed for enabling a male subject to simulate a natural penile erection. Typically, one or more longitudinally extending expansible sacs are implanted in the penis and connected through a fluid system having check valves to a fluid filled bulb that can be massaged externally for pumping the fluid into the sac to thereby simulate the natural process. Some implants cause permanent erections. Implantation of some of the artificial devices result in permanent destruction of the nerve and blood vessel passages such that a natural erection can never again be obtained. All the implant techniques require the subject to spend some time in a hospital. The hospital and surgical expense is known to be substantial.

In the prior art there is one device which can be applied externally of the penis for maintaining, but not attaining, an erection. The device is called a pubis ring. It is intended for use primarily by those males who, when excited, can develop an erection but cannot maintain it for a long enough time to satisfy themselves and their mate during intercourse. The pubis ring is designed to keep the blood in the penis once it has been pressurized by natural reaction to sexual stimuli. It cannot help in cases where there is a minimal erection or none at all. The pubis ring comprises a loop whose opposite ends enter the opposite ends of a flexible sleeve. The two ends emerge together out of a radial hole in the sleeve. The loop is slipped back to the root of the penis at a time when the subject perceives as a result of prior experience that his erection is likely to be at its maximum even though he may remember that there were times in the past when it could become larger and more rigid. When maximum is perceived, the cords of the loop are snubbed to trap the pressurized blood in the penis. The erection can then be maintained for its intended purpose. Disadvantages of the pubic ring are that it requires some dexterity to secure and focusing attention on the securing problem can be distracting enough to cause the tentative erection to disappear prior to usage.

SUMMARY OF THE INVENTION

One object of the invention is to provide a device that not only helps a male to maintain an erection when natural processes have provided one but also permits attaining and maintaining an erection where, for possibly unknown reasons, the natural process of filling the penis caverns with pressurized blood and restricting the outflow does not occur. A further object of the invention is to provide an erection obtaining and maintaining device that, in one form, not only assists the male, but, in addition, provides for massaging the female clitoris so as to enhance the pleasure of the event.

A still further object is to provide an accessory that enables the male to put the new penis conditioning device in a state of readiness for prompt use when the occasion arises.

Briefly stated, the basic form of the erection assisting device comprises an elastic ring centered between two elastic loops which are attached to the periphery of the ring on its opposite sides or at the first and third quadrants of the ring. The loops are used to stretch the ring radially outwardly to enlarge its opening sufficiently for it to fit over the root of the penis where it is released and contracts to pinch off the blood vessels leading to and from the penis. The user must then massage blood forwardly into the penis by strokes applied with the hand and fingers beginning substantially rearwardly of the scrotum to thereby develop local blood pressure sufficient to overcome the sealing force of the ring and pressurize the caverns in the penis which results in an erection.

Another form of the device has loops attached at all four quadrants of the ring, the loops in the first and third quadrants being used for applying it to the penis and a loop in the second quadrant being positioned for massaging the vagina over the clitoris during coition.

An accessory is also provided which facilitates storing the device with its elastic ring pre-stretched or expanded on a rigid ring that can be placed on the penis so the elastic ring can be easily transferred to the root of the penis.

How the foregoing objects and other more specific objects of the invention are achieved will become evident in the more detailed description of embodiments of the new device which will now be set forth in reference to the drawing.

DESCRIPTION OF A PREFERRED EMBODIMENT

Figure 1:
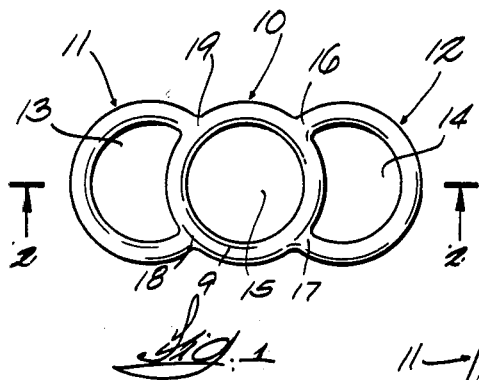
FIG. 1 is a plan view of one embodiment of the new male organ erection obtaining and maintaining device.

In FIG. 1 one may see that the first embodiment of the erection obtaining and maintaining device comprises a central elastic ring 10 and a pair of laterally extending integral elastic loops 11 and 12. The central ring 10 should be round but loops 11 and 12 need not be substantially semicircular as shown but could be almost any shape such as a 3-sided square that would provide for openings 13 and 14 into which the fingers may be entered for expanding the central ring. The central ring has an opening 15 which allows it, when expanded, to be passed over the penis down to its root. It is desirable to have the ends 16, 17, 18 and 19, for example, of the loops join with the periphery of the central ring in horizontal plans substantially above and below a parallel horizontal plane through the center of ring 10 so that when the loops are stretched laterally the central ring will expand or open more symmetrically. In geometrical terms, one loop is in the first quadrant of the ring 10 and the other is in the third quadrant. Thus, the four points of connection 16, 17 and 18, 19 between loops 12 and 11, respectively, and central ring 10 are equiangularly spaced around the ring 10 so the ring will stretch out more uniformly in response to stress created by the loops.

Figure 2:
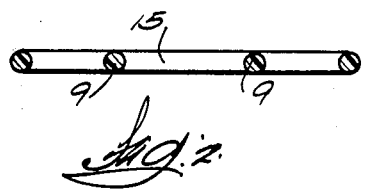
FIG. 2 is a sectional view taken on a line corresponding with 2—2 in FIG. 1.

The device in FIG. 1 is molded of an elastomeric material such as natural or silicone or other synthetic rubber having a durometer number in the range of 40 to 60. A durometer number of about 55 is preferred. The central ring 10 must have an appropriate rim 9 thickness and opening 15 diameter to adapt properly to all males. Thus, large, medium and small sizes should be provided. By way of example and not limitation, in presently available devices, one size, when still unstretched, provides an opening 15 having a diameter of 0.938 of an inch and the diameter of the rim for ring 10 which is shown in section in FIG. 2, is on the order of 0.156 of an inch. Thus, the total outside diameter of central ring 10 is about 1.1 inches. In two other sizes, the diameters of the opening in rings 10 are 0.813 and 0.688 of an inch, respectively. In these two sizes, the diameter of the cross-section of the rim 9 is again about 0.156 of an inch. The diameter and tension in the inner ring 10 is critical relative to the user's penis since the inner ring is ultimately slipped over the penis to its root where it must develop enough radially inward compressive force to prevent venous blood from emerging from the penis after arterial blood is forced into its caverns prior to use of the erected organ.

Figure 3:
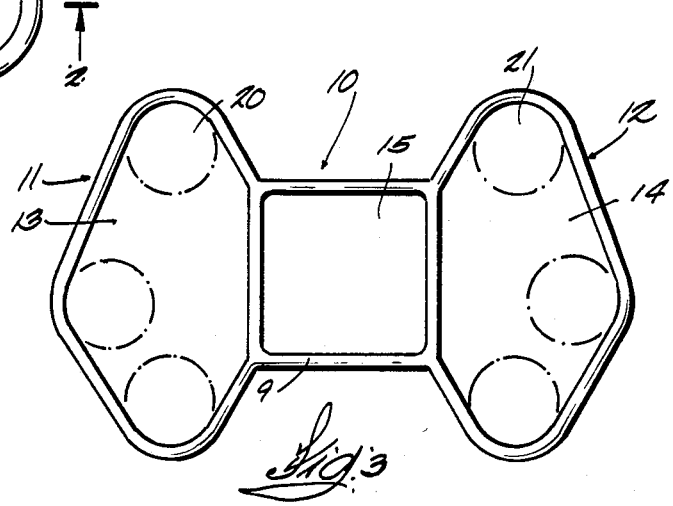
FIG. 3 is a view of the device in FIG. 1 distended by use of the fingers of the hand to a condition wherein it is ready for being placed over the penis and located at its root.

The device, prepared for application to the penis, is depicted in FIG. 3. To use the device, two or three fingers 20 on the left hand and a similar number of fingers 21 on the right hand are inserted in the outside loops 11 and 12, respectively, after which the fingers are spread simply for the purpose of enlarging the vertical dimension of the hole 15 in central ring 10. Simultaneously, the left and right hands are spread away from each other to increase the lateral dimension of hole 15. After having been stretched orthogonally, the central ring 10 is passed over the penis to its root and the fingers are removed. Due to the elasticity of the rim 9 in the originally circular central ring 10, the ring contracts to a circular form again when the stretching force of the fingers is removed. If the proper size has been chosen, the central ring 10 contracts sufficiently to inhibit normal ingress and egress of blood to and from the penis.

After the device is installed as just described, the prospective user deposits his fingers in the crotch some distance behind the scrotum and performs a forwardly massaging action to induce forward blood flow and overcome the restrictive radially inward compressive force of central ring and thereby force blood into the previously mentioned caverns of the penis. The massaging action is repeated until the penis becomes satisfactorily large and rigid in which case it is ready for coition. Although the massaging action will force blood to the penis, it cannot back flow because of the relatively high tension of the rim 9 forming center ring 10. The device acts as a check valve.

Figure 4:
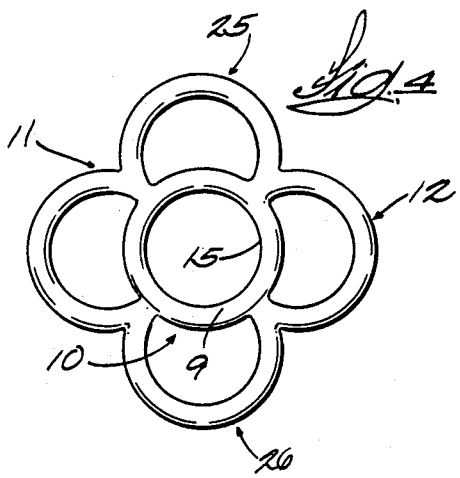
FIG. 4 is a plan view of an alternative form of the organ conditioning device.

FIG. 4 shows another embodiment of the device wherein parts that are similar to those in FIG. 1 are given the same reference numerals. Thus, there is a central ring 10 having a hole 15 and two laterally extending loops 11 and 12. In this embodiment, there are two additional vertically arranged loops 25 and 26. They are in the second and fourth quadrants relative to ring 10. In other words one pair of loops are orthogonal relative to the other pair. When the central ring 10 is installed on the penis as previously described in reference to FIG. 3, the user desirably arranges loops 25 and 26 in a vertical attitude, that is, directly above and directly below the root of the penis. This contemplates having the loops 25 and 26 aligned with the vagina of the female such that during coition, whichever of the loops 25 or 26 is on top, will exert some pressure on the region containing the clitoris which can be massaged and stimulated by movements of the loop. Of course, one of the loops 25 or 26 could be eliminated at the expense of making the device unsymmetrical. Loops 25 or 26 could also be narrower than the other loops.

Figure 5:
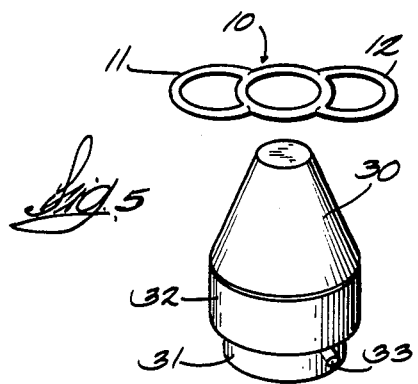
FIG. 5 shows the device of FIG. 1 associated with an accessory for putting the device into a condition for application to the penis.
Figure 6:
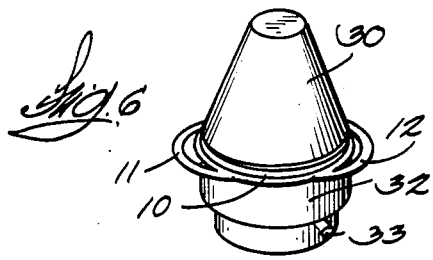
FIG. 6 is comparable to the preceding figure except that the conditioning device is installed on the accessory; and, FIG. 7 shows the organ conditioning device set on a ring that has been removed from the accessory such that the ring may be slid to the root or base of the penis and the device rolled off of it for performing its blood capturing function.
Figure 7:
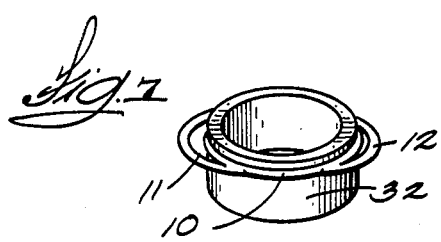

An accessory is depicted in FIGS. 5-7 for making use of the erection obtaining and maintaining device more convenient and prompt as circumstances dictate. The accessory body is composed of a conical portion 30 and a coaxial integral cylindrical portion 31. These parts may be molded unitarily with a thermosetting resin. The diameter of the cylinder is less than the diameter of the base of the cone to thereby create a shoulder. A plastic sleeve 32 fits over cylindrical portion 31 and is retained by a tapered pin 33 which fits into a mating hole in cylinder 31. The outside diameter of the sleeve is no greater than the cone base diameter. As shown in FIG. 5, the central ring 10 of the device is aligned with the apex of cone 30 and is brought down and slid over the cone to expand the central elastic ring 10 for it to slide onto rigid plastic sleeve 32. It has been found that wetting the ring or the cone makes it more slippery and facilitates sliding it along the cone onto the rigid sleeve more easily.

After the elastic ring is slid onto rigid plastic sleeve 32, pin 33 is removed and sleeve 32 can be withdrawn with elastic ring 10 of the device deposited on it as in FIG. 7. The internal diameter of plastic sleeve 32 is sufficient for the plastic ring to slide freely over the male penis. It is desirable to have the elastic ring 10 of the device deposited at one axial end of the rigid sleeve 32 so that when this end is brought up against the body adjacent the root of the penis, the ring 10 and the entire device can be rolled off the rigid sleeve to deposit the device on the penis.

One of the merits of the accessory depicted in FIGS. 5–7 is that the installation of the elastic ring 10 on rigid sleeve 32 can be done far in advance of expected use of the device so it will be ready for quick and easy installation on the penis when its use is desired. The device can be mounted on rigid sleeve 32 as shown in FIG. 7 and carried in the pocket of a male who contemplates its use in the not too distant future without having to carry along the conical accessory body to the site of use. In fact, extra sleeves may be made available to permit mounting more than one device on a rigid sleeve in case a situation develops requiring a sequence of uses of the device at a site remote from where the accessory body is stored.

Although preferred embodiments of the male organ conditioner device have been described in detail, such description is intended to be illustrative rather than limiting, for the invention may be variously embodied and is to be limited in scope only by interpretation of the claims which follow.

I claim:

1. A device for developing and maintaining an erect penis, comprising:
    a ring composed of elastic material having a circular outer periphery and defining a uniformly round inside opening when said ring is unstretched,
    a pair of loops composed of said elastic material, said loops being joined integrally with said outer periphery of the ring generally diametrically opposite of each other for being engaged to impart a stretching force to said ring generally radially outwardly to enlarge said inside opening sufficiently for said ring to be slipped over the penis to the root thereof such that when said stretching force is relieved residual elastic force in said ring is sufficient to allow blood to be manually massaged into the penis and to prevent outflow of blood from the penis.

2. The device according to claim 1 wherein said loops have ends that join with the periphery of said ring portion at locations that are substantially equiangularly spaced around said ring portion.

3. The device according to claim 1 wherein said loops have a generally semicircular configuration.

4. The device according to claim 1 including a loop joined to the periphery of said ring portion between the loops in said pair.

5. The device according to any one of claims 1, 2, 3 or 4 wherein the elastic material composing said ring and each loop is a material selected from the class consisting of natural rubber, synthetic rubber and silicone rubber.

6. The device according to any one of claims 1, 2, 3 or 4 wherein the inside diameter of said ring portion is in the range of about 0.68 to 0.93 of an inch, the diameter of a section through said ring portion is about 0.15 of an inch, and said elastic material composing said ring portion is one selected from the class of natural, synthetic and silicone rubber having a durometer number within the range of 40 to 60.

7. The device according to claim 6 wherein the durometer number of said material is about 55.

8. A device for obtaining and maintaining penile erection comprising:
    a ring having a round inside opening and a first pair of loops all composed of elastic material, each of said loops being joined with the periphery of said ring generally diametrically opposite of each other and extending generally radially outwardly from the ring such that said loops may be manually engaged to stretch the ring generally radially outwardly to enlarge said opening for said ring to be slipped over the penis to its root where said ring is allowed to contract to develop a compressive force that permits blood to be massaged into the penis and prevents outflow therefrom,
    a second pair of loops comprised of the same material as said first pair, each loop in said second pair joined to the periphery of said ring orthogonally of and between the loops in said first pair,
    the inside diameter of said ring opening being in the range of about 0.68 to 0.93 of an inch, the diameter of a section through said ring being about 0.15 of an inch, and said elastic material composing said ring is one selected from the class of material, synthetic and silicone rubber having a durometer number within the range of 40 to 60.

* * * * *